(12) United States Patent
Chatterjee et al.

(10) Patent No.: US 8,916,713 B2
(45) Date of Patent: Dec. 23, 2014

(54) PROCESS FOR THE PREPARATION OF FEBUXOSTAT

(75) Inventors: Pranab Chatterjee, Nadia (IN); Asok Nath, Gurgaon (IN); Sarbjot Singh Sokhi, Amritsar (IN); Mohan Prasad, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 54 days.

(21) Appl. No.: 13/812,066

(22) PCT Filed: Jul. 15, 2011

(86) PCT No.: PCT/IB2011/053171
§ 371 (c)(1),
(2), (4) Date: Mar. 28, 2013

(87) PCT Pub. No.: WO2012/014117
PCT Pub. Date: Feb. 2, 2012

(65) Prior Publication Data
US 2013/0245278 A1    Sep. 19, 2013

(30) Foreign Application Priority Data
Jul. 30, 2010  (IN) .......................... 1805/DEL/2010

(51) Int. Cl.
*C07D 277/56*    (2006.01)
(52) U.S. Cl.
CPC ................................... *C07D 277/56* (2013.01)
USPC ....................................................... 548/201

(58) Field of Classification Search
CPC ...................................................... C07D 277/56
USPC ............................................................ 548/201
See application file for complete search history.

(56) References Cited

U.S. PATENT DOCUMENTS 5,614,520 A    3/1997  Kondo et al. .............. 514/236.8

FOREIGN PATENT DOCUMENTS

| JP | 06329647 A | * 11/1994 | |
| JP | 2-706037 | 1/1998 | A61K 31/425 |
| JP | 10-139770 | 5/1998 | B01J 31/22 |
| JP | 2-834971 | 12/1998 | C07D 277/20 |
| JP | 3-169735 | 5/2001 | A61K 31/425 |
| JP | 3-202607 | 8/2001 | C07D 277/20 |
| WO | WO 2011/031409 | 3/2011 | C07D 277/20 |
| WO | WO 2011/073617 | 6/2011 | C07D 277/56 |
| WO | WO 2011101867 A2 * | 8/2011 | |

OTHER PUBLICATIONS

Sigma-Aldrich MSDS for barium hydroxide monohydrate, revision date Sep. 25, 2013.*
Fisher Scientific MSDS for barium hydroxide, anhydrous, revision date Jul. 20, 2009.*
Machine translation of the description of JP 06329647 A by Watanabe et al., obtained from http://www4.ipdl.inpit.go.jp/Tokujitu/tjsogodbenk.ipdl on May 18, 2014.*
Hasegawa, "A Facile One-Pot Synthesis of 4-Alkoxy-1,3-Benzenedicarbonitrile", *Heterocycles*, 47(2):857-864 (1998).

* cited by examiner

*Primary Examiner* — Joseph Kosack
*Assistant Examiner* — Matthew Coughlin

(57) ABSTRACT

An improved and efficient process for the preparation of 2-[3-cyano-4-(2-methylpropoxy)phenyl]-4-methylthiazole-5-carboxylic acid (febuxostat) that is substantially free from amide by-product is provided.

6 Claims, No Drawings

PROCESS FOR THE PREPARATION OF FEBUXOSTAT

FIELD OF THE INVENTION

An improved and efficient process for the preparation of 2-[3-cyano-4-(2-methylpropoxy)phenyl]-4-methylthiazole-5-carboxylic acid (febuxostat) that is substantially free from amide by-product is provided.

BACKGROUND OF THE INVENTION

Febuxostat is a non-purine xanthine oxidase inhibitor known from U.S. Pat. No. 5,614,520. It is chemically designated as 2-[3-cyano-4-(2-methylpropoxy)phenyl]-4-methylthiazole-5-carboxylic acid having the structure as represented by Formula I.

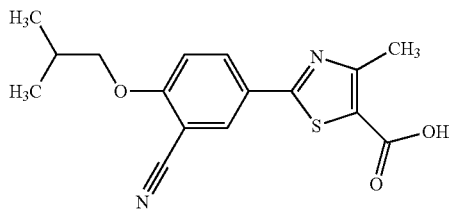

Formula I

Febuxostat is marketed in the United States under the brand name Uloric® and in Europe under the brand name Adenuric® for the chronic management of hyperuricemia in patients with gout. It works by non-competitively blocking the channel leading to the active site on xanthine oxidase. Xanthine oxidase is needed to successively oxidate both hypoxanthine and xanthine to uric acid. Hence, febuxostat inhibits xanthine oxidase, therefore, reducing production of uric acid.

Processes for the preparation of febuxostat and intermediates thereof are disclosed in U.S. Pat. No. 5,614,520; Japanese Patent Nos. JP 2834971; JP 3202607; JP 2706037, JP 10139770 and JP 3169735.

U.S. Pat. No. 5,614,520 discloses preparation of febuxostat by hydrolysis of its corresponding ester using sodium hydroxide. It has been observed that when hydrolysis is carried out with sodium hydroxide, the cyano moiety also gets hydrolyzed along with ester leading to the generation of amide by-product, a very potential impurity in febuxostat API. The structure of the amide by-product is as shown below:

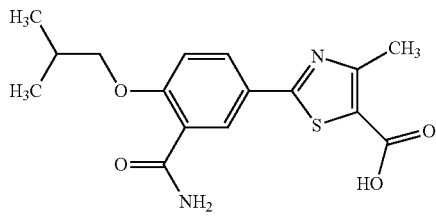 [SMILES: Cc1nc(-c2ccc(OCC(C)C)c(C(N)=O)c2)sc1C(=O)O]

JP 2834971 describes preparation of febuxostat ester via formylation of a 4-hydroxyphenyl substituted thiazole intermediate in the presence of an organic acid, preferably with trifluoroacetic acid, and JP 3202607 describes preparation of febuxostat ester via formylation of a 4-hydroxyphenyl substituted thiazole intermediate in the presence of polyphosphoric acid. The work-up procedure for the isolation of product is tedious requiring a number of steps.

The processes described in U.S. Pat. No. 5,614,520, JP 2706037, JP 10139770 and JP 3169735 involve the use of toxic metal cyanides for the preparation of febuxostat. The use of metal cyanides is hazardous to health and is not recommended for an industrial scale preparation.

Accordingly, there is a need for a process to synthesize febuxostat that is substantially free of the amide by-product. The process should avoid long work-up procedures and allow easy isolation of final product and also avoid the use of toxic metal cyanides.

SUMMARY OF THE INVENTION

The present invention provides an improved and efficient manufacturing method of 2-[3-cyano-4-(2-methylpropoxy)phenyl]-4-methylthiazole-5-carboxylic acid (febuxostat) that addresses many of the drawbacks of the prior art processes. Thus, it is suitable for commercial-scale production. The process of the present invention does not involve the use of hazardous cyanides. Also, the process makes use of methanesulfonic acid for formylation, which allows easy isolation of the formylated product. In addition, the febuxostat so synthesized is substantially free from the amide by-product. The control of the formation of amide by-product was a challenge. The inventors of this patent application found that this amide by-product could be controlled by selecting appropriate base and solvent for the hydrolysis step.

Accordingly, the first aspect of the present invention provides a process for the preparation of febuxostat of Formula I

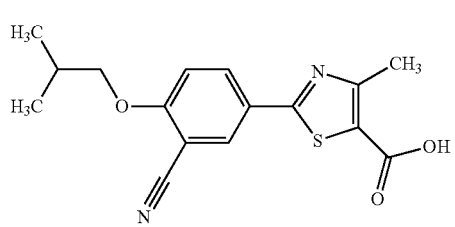

Formula I comprising the steps of:
(i) reacting 4-hydroxy thiobenzamide of Formula II

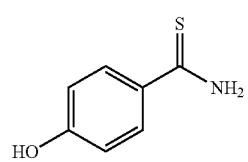

Formula II with a compound of Formula III (wherein X is halogen and R is alkyl or arylalkyl)

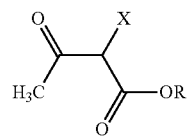

Formula III to give a compound of Formula IV;

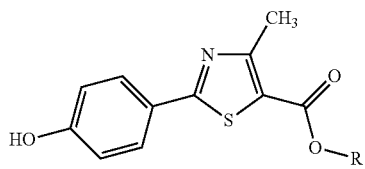

Formula IV (ii) formylation of the compound of Formula IV with hexamethylene tetramine in presence of an acid to give a compound of Formula V;

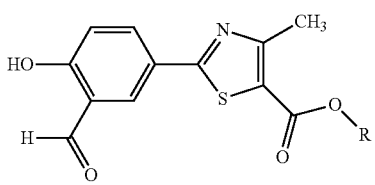

Formula V (iii) reaction of the compound of Formula V with hydroxylamine hydrochloride to give a compound of Formula VI;

Formula VI

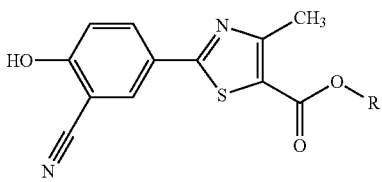

(iv) alkylation of the compound of Formula VI with isobutyl halide of Formula VII (wherein X is halogen)

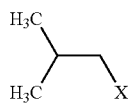

Formula VII to give a compound Formula VIII; and

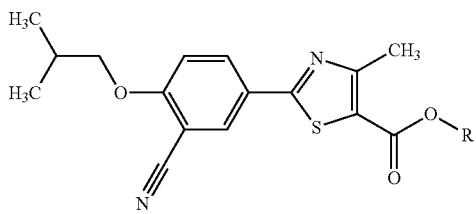

Formula VIII (v) hydrolysis of the compound of Formula VIII with a base selected from oxide and hydroxide of barium to give febuxostat of Formula I.

In a second aspect, the present invention provides a process for the preparation of febuxostat of Formula I

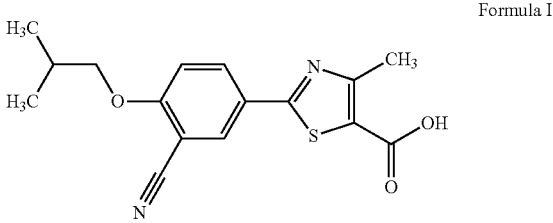 [SMILES: Cc1nc(-c2ccc(OCC(C)C)c(C#N)c2)sc1C(=O)O]

Formula I comprising hydrolysis of the compound of Formula VIII (wherein R is ethyl)

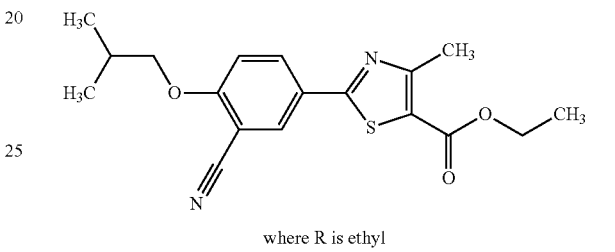

Formula VIII where R is ethyl with barium hydroxide octahydrate.

Other objects, features, advantages and aspects of the present invention will become apparent to those of ordinary skill in the art from the following detailed description.

DETAILED DESCRIPTION OF THE INVENTION

Definitions

The following definitions apply to terms as used herein:

The term "alkyl", unless otherwise specified, refers to a monoradical branched or unbranched saturated hydrocarbon chain having from 1 to 20 carbon atoms. This term can be exemplified by groups such as methyl, ethyl, n-propyl, iso-propyl, n-butyl, iso-butyl, sec-butyl, t-butyl, n-pentyl, isopentyl, neopentyl, n-hexyl, n-decyl, tetradecyl, and the like.

The term "arylalkyl", unless otherwise specified, refers to alkyl-aryl linked through an alkyl portion (wherein alkyl is as defined above) and the alkyl portion contains 1-6 carbon atoms and aryl is as defined below. Examples of arylalkyl groups include benzyl, ethylphenyl, propylphenyl, naphthylmethyl, and the like.

The term "halogen" or "halo" or "halide" refers to fluorine, chlorine, bromine or iodine.

The term "substantially free from amide by-product" refers to limit of amide by-product in febuxostat of Formula I as less than or equal to 0.07%.

Various embodiments and variants of the present invention are described hereinafter.

The reaction of a compound of Formula II with a compound of Formula III (wherein X is halo and R is alkyl or arylalkyl) to give a compound of Formula IV can be carried out in a solvent, for example, ethanol, methanol, denatured spirit (DNS), 2-propanol, 2-methyl-2-propanol or the mixture(s) thereof, at a temperature of about 0° C. to about 250° C. for about 15 minutes to about several days depending on type of reactant and solvent selected.

In a particular embodiment, the reaction of compound of Formula II with a compound of Formula III (wherein X is Cl and R is ethyl) to give a compound of Formula IV is carried out in denatured spirit (DNS) at a temperature of about 60° C. to about 65° C. for a time period of about 2.5 hours.

The formylation of the compound of Formula IV with hexamethylene tetramine to give a compound of Formula V can be carried out in presence of an acid selected from methanesulfonic acid, trifluoroacetic acid, polyphosphoric acid, ethane sulphonic acid, trifluoromethane sulphonic acid, p-toluene sulphonic acid, acetic acid, formic acid, propionic acid, or mixture(s) thereof, optionally in the presence of a solvent, for example, benzene, toluene, dichloromethane, dichloroethane, chloroform, carbon tetrachloride, ethyl acetate, methanol, ethanol, propanol, 2-propanol, diethylether, tetrahydrofuran, dioxane, 1,2-dimethoxyethane, dimethylformamide, dimethyl sulfoxide, or mixture(s) thereof, at a temperature of about 0° C. to about 250° C. for about 15 minutes to about several days depending on type of reactant, solvent and acid selected. After completion of the reaction, the reaction mixture may be cooled. The isolation of product can be carried out by addition of a solvent, for example, water and then optional extraction in a different solvent, for example, ethyl acetate. In a particular embodiment, the formylation of compound of Formula IV (wherein R is ethyl) is carried out with methanesulfonic acid at a temperature of about 20° C. to about 100° C. for a time period of about 10 hours to about 14 hours.

In a particular embodiment, the formylation of compound of Formula IV is carried out by adding hexamethylene tetramine to a solution of hydroxy phenyl thiazole ethyl ester in methanesulfonic acid over an interval of about 30 minutes. The reaction mixture may be heated at a temperature of about 70° C. to about 80° C. for a period of about 10 hours to about 12 hours. The reaction mixture may be cooled to about 30° C. Isolation of the product may be carried out by adding water, cooling to about 0° C. to about 5° C. and stirring for about another 1 hour.

The conversion of the compound of Formula V to a compound of Formula VI can be carried out with hydroxylamine hydrochloride, wherein formyl group reacts with hydroxylamine initially to form oxime and then a cyano group. The reaction can be carried out in a solvent, for example, formic acid, acetic acid, dichloromethane, dichloroethane, chloroform, carbon tetrachloride, methanol, ethanol, 1-propanol, 2-propanol, toluene, benzene, pyridine, ethyl acetate, diethylether, tetrahydrofuran, dioxane, 1,2-methoxyethane, dimethylformamide, dimethyl sulfoxide, or mixture(s) thereof, in the presence of a base, for example, sodium formate, potassium formate, sodium acetate, triethylamine, potassium carbonate, caesium carbonate, sodium carbonate, sodium bicarbonate, pyridine or mixture(s) thereof at a temperature of about 0° C. to about 250° C. for about 15 minutes to about several days depending on type of reactant, solvent and base selected.

In a particular embodiment, the reaction of compound of Formula V (wherein R is ethyl) with hydroxylamine hydrochloride to give a compound of Formula VI is carried out using sodium formate as base and formic acid as solvent at a temperature of about 25° C. to about 125° C. for a time period of about 7 hours to about 12 hours.

The alkylation of the compound of Formula VI with isobutyl halide of Formula VII to give a compound of Formula VIII can be carried out in the presence of a base, for example, potassium carbonate, sodium carbonate, caesium carbonate, sodium bicarbonate, sodium hydride, a sodium ethoxide, sodium methoxide, potassium tert-butoxide, triethylamine or pyridine, optionally in the presence of an additive agent, for example, potassium iodide, sodium iodide or dimethylaminopyridine (DMAP), in a solvent, for example, dimethylformamide, dimethylacetamide, ethyl methyl ketone, acetone, methyl isopropyl ketone, methyl isobutyl ketone, methyl n-butyl ketone, methyl t-butyl ketone, methyl isoamyl ketone, dimethyl sulfoxide, hexamethylphosphoric triamide, tetrahydrofuran, dioxane, dimethoxyethane, diethylene glycol, dimethyl ether, dichloromethane, dichloroethane, chloroform, carbon tetrachloride, toluene, ethyl acetate, or mixture(s) thereof. The temperature of the reaction mixture may vary from about 0° C. to about 250° C. and the time interval for carrying out the reaction may vary from about 15 minutes to about several days depending upon the solvent, additive agent, base and reactants involved. In a particular embodiment, the isobutyl halide is isobutyl bromide, the solvent is dimethylformamide, the temperature for carrying out the reaction is about 70° C. to about 80° C. and the time interval is about 7 hours to about 8 hours.

The hydrolysis of the compound of Formula VIII to give febuxostat of Formula I can be carried out in the presence of a base, for example, alkali or alkaline earth metal oxides and hydroxides selected from barium hydroxide octahydrate, barium oxide, potassium hydroxide, magnesium hydroxide, lithium hydroxide or calcium hydroxide in a solvent, for example, tetrahydrofuran (THF), water, ethanol, methanol, denatured spirit, 1-propanol, 2-propanol, 1-butanol, dimethylformamide (DMF), dimethylacetamide (DMA), ethyl methyl ketone, acetone, methyl isopropyl ketone, methyl isobutyl ketone, methyl n-butyl ketone, methyl t-butyl ketone, methyl isoamyl ketone, dimethyl sulfoxide, dichloromethane, dichloroethane, chloroform, carbon tetrachloride, toluene, ethyl acetate or mixture(s) thereof at a temperature of about 0° C. to about 250° C. for about 15 minutes to about several days depending on type of reactant, solvent and base selected. In a particular embodiment, hydrolysis of compound of Formula VIII is carried out with barium hydroxide octahydrate, barium oxide or lithium hydroxide monohydrate in a solvent selected from tetrahydrofuran, ethanol, water, 2-propanol, methanol, denatured spirit, or mixture(s) thereof. In another particular embodiment, the hydrolysis of compound of Formula VIII (wherein R is ethyl) to give febuxostat of Formula I is carried out with barium hydroxide octahydrate in tetrahydrofuran, ethanol, methanol, denatured spirit and water. The temperature of the reaction may be about 55° C. to about 70° C., more particularly about 60° C. to about 65° C. The time interval for carrying out the reaction may be from about 30 minutes to about 3 hours, more particularly about 90 minutes to about 120 minutes. Upon completion of reaction, the temperature of the reaction mixture may be cooled down to about 40° C. to about 55° C. Dilution of the reaction mixture may be carried out with a solvent such as ethyl acetate and water. pH of the reaction mixture may be adjusted to 0.5-0.8 with an acid such as 6N HCl. The organic layer is separated and the aqueous layer is extracted with ethyl acetate. The combined organic layer may be treated with activated carbon, filtered and concentrated. The residue thus obtained may be dissolved in a solvent selected from dichloromethane, dichloroethane, chloroform or carbon tetrachloride, methanol, ethanol, 2-propanol, 1-propanol, 2-methyl-2-propanol, or mixture(s) thereof. The solution may be cooled to about 0° C. to about 10° C., more particularly to about 0° C. to about 5° C., stirred for about 1 hour, filtered, washed with a pre-cooled mixture of methanol and dichloromethane and dried under reduced pressure to febuxostat.

The hydrolysis process of the present invention uses barium hydroxide octahydrate and thereby provides febuxostat of very high chemical purity with very less amount of amide by-product as compared to conventional hydrolyzing agents. The experimental observations are tabulated in Table 1 as below.

TABLE 1

| Base Used | Solvent used | Amide by-product in the reaction | Isolated product HPLC purity | Amide by-product |
|---|---|---|---|---|
| NaOH (1.7 mole eqv) (As per patent U.S Pat. No. 5,614,520) | Mixture of THF and absolute alcohol | 0.34% | 99.80% | 0.15% |
| NaOH solution (1.7 mole eqv) | THF | 0.27% | 99.85% | 0.15% |
| Ba(OH)$_2$•8H$_2$O solution (0.6 mol eqv) | Mixture of THF and IPA | 0.21% | 99.90% | 0.10% |
| Ba(OH)$_2$•8H$_2$O solution (0.6 mol eqv) | Mixture of THF and absolute alcohol | 0.158% | 99.93% | 0.07% |
| Ba(OH)$_2$•8H$_2$O solution (0.6 mol eqv) | Mixture of THF and DNS | 0.14% | 99.87% | 0.07% |
| BaO solution (0.6 mol eqv) | Mixture of THF and absolute alcohol | 0.12% | 99.89% | 0.06% |
| BaO solution (1 mol eqv) | Mixture of THF and methanol | 0.25% | — | — |

It has also been observed that the formation of amide by-product increases with time in case of hydrolysis with conventional hydrolyzing agents such as sodium hydroxide, whereas in case of the hydrolysis with barium hydroxide octahydrate, the amide by-product does not increase with time as shown below in Table 2.

TABLE 2

| Base Used | Solvent used | Reaction Time | Formation of Amide by-product in the reaction Amide by-product |
|---|---|---|---|
| NaOH Solution (1.7 mole equivalent) | Mixture of THF and absolute alcohol | 45 min | 0.24% |
| | | 2 hrs | 0.38% |
| | | 3 hrs | 0.53% |
| | | 4 hrs | 0.62% |
| | | 5 hrs | 0.79% |
| NaOH (1.7 mole equivalent) | Mixture of THF and absolute alcohol | 1 hr | 0.44% |
| | | 2 hrs | 0.50% |
| | | 3 hrs | 0.68% |
| | | 4 hrs | 0.84% |
| | | 5 hrs | 0.95% |
| Ba(OH)$_2$•8H$_2$O (0.6 mole equivalent) | Mixture of THF and absolute alcohol | 6 hrs | <0.10% |
| | | 7 hrs | 0.10% |
| | | 8 hrs | 0.10% |
| | | 22 hrs | 0.16% |

In the present invention, reactants may interact with each other by different means, for example, dissolving to give a solution, slurrying to form a suspension or making colloids to give an emulsion.

In the present invention, isolation of the product may be accomplished by, among other things, extraction, concentration, precipitation, crystallization, filtration or centrifugation.

Washing of the obtained residue may be carried out using the solvents in which the product is sparingly soluble and by selecting a temperature that allows dissolving of impurities only and not the desired product. The solvents for washing may include, but are not limited to, water, ethyl acetate, acetone, methanol, ethanol, 1-propanol, 2-propanol, 1-butanol, 2-butanol, 2-methyl-l-propanol, 1-pentanol, ethylene glycol, propylene glycol, diethyl ether, ethyl methyl ether, tert-butyl methyl ether, tetrahydrofuran or 1,4-dioxane, methyl acetate, propyl acetate, butyl acetate, methyl ethyl ketone, methyl isobutyl ketone, benzene, toluene, xylene, N,N-dimethylformamide or N,N-dimethylacetamide, acetonitrile, propionitrile, dimethyl sulfoxide, diethyl sulphoxide, or mixture(s) thereof.

Extraction of the product is a method to separate compounds based on their relative solubilities in two different immiscible liquids, usually water and an organic solvent, and may be carried out using a separatory funnel. The extraction process in the present invention may employ non-aqueous systems also depending upon the type of product. Extraction process may be single stage or a multistage continuous process.

Separation and concentration method of the organic compound should be such that allows minimum product decomposition and maximum product quality. The methods for concentration employed in the present invention may involve any of the conventional methods known in the art, for example, common distillation, distillation under reduced pressure, through reverse osmosis membrane, prevaporation through a membrane, hydrophilic ultrafiltration membrane, or a combination thereof.

Drying may be accomplished by any suitable method of drying such as drying under reduced pressure, vacuum tray drying, air drying or a combination thereof. Drying may be carried out at a temperature of about 45° C. to about 70° C. for about 10 hours to about 2 days.

Filtration may be accomplished by any of the methods known in the art, for example, by using büchner funnel, belt filter, rotary vacuum-drum filter, crossflow filters, screen filter. Filtration may also be accompanied by filter aids, for example, diatomaceous earth, kieselguhr, wood cellulose, perlite, etc. or a combination thereof.

Purification or refinement may be accomplished by combining suitable means, such as processing by extraction, chromatography separation, activated carbon, florisil, etc., and recrystallization.

In the foregoing section, embodiments are described by way of examples to illustrate the processes of invention. However, these are not intended in any way to limit the scope of the present invention. Several variants of the examples would be evident to persons ordinarily skilled in the art which are within the scope of the present invention.

Non-limiting examples of the present invention are as follows.

EXAMPLES

Example 1

Synthesis of Ethyl 2-(4-Hydroxyphenyl)-4-Methyl-5-Thiazol Carboxylate

A mixture of 4-hydroxy thiobenzamide (100 g, 0.653 mol) and ethyl 2-chloroacetoacetate (118.3 g, 0.719 mol) in denatured spirit (DNS) (500 mL) was heated at about 60° C. to 65° C. for about 2.5 hours. The reaction mixture was cooled to about 0° C. to 5° C. and stirred for about 1 hour at the same temperature. The solid obtained was filtered, washed with denatured spirit and dried to obtain the title compound. (Yield: 156 g, 90.7%)

Example 2

Synthesis of Ethyl-2-(3-Formyl-4-Hydroxyphenyl)-4-Methyl-5-Thiazole Carboxylate Hexamethylene tetramine (134 g, 0.971 mol) was added to a solution of ethyl 2-(4-hydroxyphenyl)-4-methyl-5-thiazol carboxylate (100 g, 0.38 mol) in methanesulfonic acid (500 mL) slowly over a period of about 30 minutes. The reaction mixture was heated to about 75° C. and stirred for about 10 hours. After completion of reaction, the reaction mixture was cooled to about 30° C. and water was added to it. The reaction mixture was further cooled to about 0° C. and stirred for about 1 hour. The solid thus obtained was filtered, washed with water and dried to give the title compound. (Yield: 80 g, 72.3%)

Example 3

Synthesis of ethyl-2-(3-cyano-4-hydroxyphenyl)-4-methyl-5-thiazole carboxylate Hydroxylamine hydrochloride (35.82 g, 0.515 mol) and sodium formate (46.73 g, 0.687 mol) were added to a solution of ethyl-2-(3-formyl-4-hydroxyphenyl)-4-methyl-5-thiazole carboxylate (100 g, 0.343 mol) in formic acid (anhydrous, 300 mL) and the reaction mixture was heated to a temperature of about 100° C. for about 8 hours. After completion of reaction, the reaction mixture was cooled to about 40° C. and water was added to it. The reaction mixture was cooled to about 25° C. and stirred for about 1 hour. The solid obtained was filtered, washed with water and dried. The solid was then dissolved in acetone at about 50° C. and water was added slowly over a period of about 30 minutes. The mixture was cooled to about 25° C. and again stirred for about 1 hour. The solid thus obtained was filtered, washed with acetone:water (1:1) mixture and dried to obtain the title product. (Yield: 85 g, 85.9%)

Example 4

Synthesis of Ethyl-2-(3-Cyano-4-Isobutyloxyphenyl)-Methyl-5-Thiazole Carboxylate Potassium carbonate (300 g, 2.17 mol) and isobutyl bromide (142.7 g, 1.041 mol) were added to a solution of ethyl-2-(3-cyano-4-hydroxyphenyl)-4-methyl-5-thiazole carboxylate (100 g, 0.347 mol) in dimethylformamide (300 mL), and the reaction mixture was heated at a temperature of about 75° C. for about 8 hours. After completion of reaction, the reaction mixture was cooled to about 40° C. and water was added. The reaction mixture was further cooled to about 0° C. and stirred for about 1 hour. The solid thus obtained was filtered, washed with water and dried to give title compound. (Yield: 111g, 92.9%)

Example 5

Synthesis of 2[3-Cyano-4-(2-Methylpropoxy)Phenyl]-4-Methylthiazole-5-Carboxylic Acid (Febuxostat)

Aqueous barium hydroxide octahydrate solution (prepared by dissolving 55 g, 0.174 mol of barium hydroxide octahydrate in 350 mL water) was added to a solution of ethyl-2-(3-cyano-4-isobutyloxyphenyl)-4-methyl-5-thiazole carboxylate (100 g, 0.29 mol) in tetrahydrofuran (1000 mL) and denatured spirit (300 mL). The reaction mixture was stirred at a temperature of about 60° C. for about 90 minutes to about 120 minutes. After completion of reaction, the mixture was cooled to a temperature of about 45° C. and diluted with ethyl acetate and water. The pH of the reaction mixture was adjusted to 0.5-0.8 with 6N HCl at about 35° C. The organic layer was separated and the aqueous layer was extracted with ethyl acetate. The combined organic layer was treated with activated carbon (10 g) and filtered through hyflobed. The hyflobed was washed with ethyl acetate. The combined filtrate was concentrated at a temperature of about 45° C. under reduced pressure. The residue thus obtained was dissolved in a mixture of dichloromethane (400 mL) and methanol (1000 mL) and the solution was cooled to about 0° C., stirred for about 1 hour. The solid thus obtained was filtered, washed with a precooled mixture of methanol and methylene chloride, dried under reduced pressure to give febuxostat. (Yield: 81 g, 88%)

HPLC purity: 99.93%

Amide by-product: 0.07%.

We claim:

1. A process for the preparation of febuxostat of Formula I

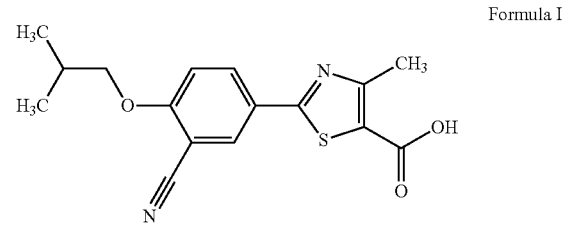 [SMILES: Cc1nc(-c2ccc(OCC(C)C)c(C#N)c2)sc1C(=O)O]

Formula I comprising the steps of:

(i) reacting 4-hydroxy thiobenzamide of Formula II

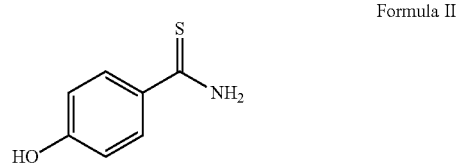

Formula II with a compound of Formula III (wherein X is halogen and R is alkyl or arylalkyl)

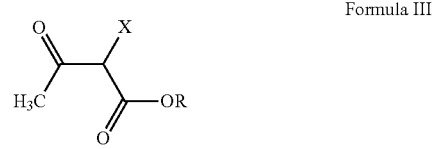

Formula III to give a compound of Formula IV;

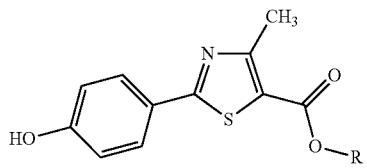
Formula IV (ii) formulation of the compound of Formula IV with hexamethylene tetramine in presence of an acid to give a compound of Formula V;

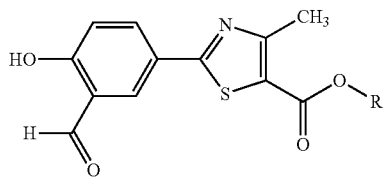
Formula V (iii) reaction of the compound of Formula V with hydroxylamine hydrochloride to give a compound of Formula VI;

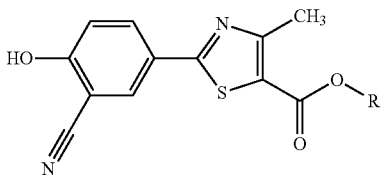
Formula VI (iv) alkylation of the compound of Formula VI with isobutyl halide of Formula VII (wherein X is halogen)

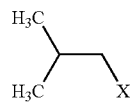
Formula VII to give a compound Formula VIII; and

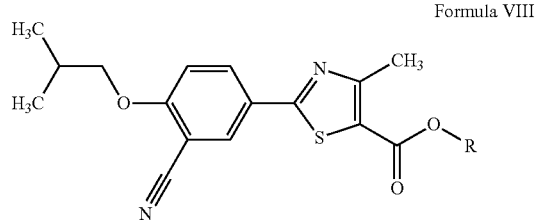
Formula VIII (v) hydrolysis of the compound of Formula VIII in the presence of barium oxide.

2. A process for the preparation of febuxostat of Formula I

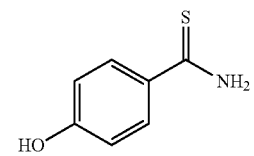
Formula I comprising the steps of:
(i) reacting 4-hydroxy thiobenzamide of Formula II

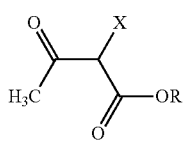
Formula II with a compound of Formula III (wherein X is halogen and R is alkyl or arylalkyl)

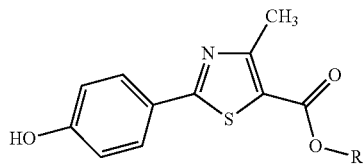
Formula III to give a compound of Formula IV;

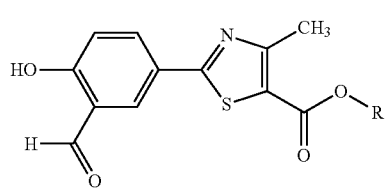
Formula IV (ii) formulation of the compound of Formula IV with hexamethylene tetramine in presence of an acid to give a compound of Formula V;

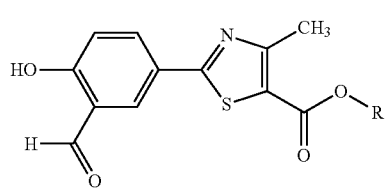
Formula V (iii) reaction of the compound of Formula V with hydroxylamine hydrochloride to give a compound of Formula VI;

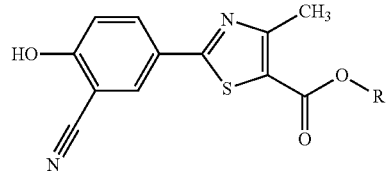

Formula VI (iv) alkylation of the compound of Formula VI with isobutyl halide of Formula VII (wherein X is halogen)

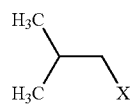

Formula VII to give a compound Formula VIII; and

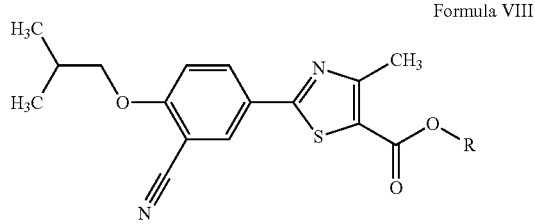

Formula VIII (v) hydrolysis of the compound of Formula VIII in the presence of barium hydroxide octahydrate.

3. A process for the preparation of febuxostat of Formula I

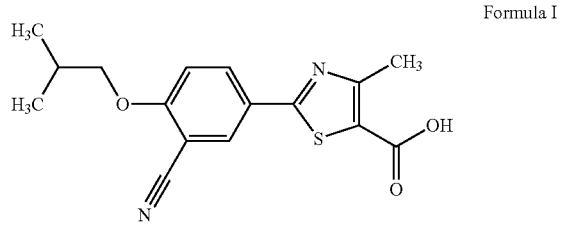 [SMILES: Cc1nc(-c2ccc(OCC(C)C)c(C#N)c2)sc1C(=O)O]

Formula I comprising hydrolysis of the compound of the following formula

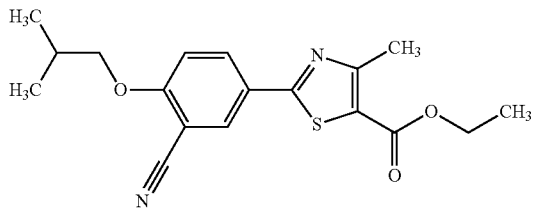 [SMILES: CCOC(=O)c1sc(-c2ccc(OCC(C)C)c(C#N)c2)nc1C]

with barium hydroxide octahydrate.

4. The process according to claim 3, wherein febuxostat of Formula I is substantially free of amide by-product.

5. The process according to claim 3, wherein febuxostat of Formula I contains 0.07% amide by-product.

6. The process according to claim 3, wherein in febuxostat of Formula I contains less than 0.07% amide by-product.

* * * * *